United States Patent [19]

Tomita et al.

[11] 4,032,588

[45] June 28, 1977

[54] PROCESS FOR PREPARING 2,6,10,15,19,23-HEXAMETHYLTETRACOSANE

[75] Inventors: Kenichi Tomita, Yokohama; Toshiaki Shibuya; Suzuko Koshiba, both of Tokyo; Kazuo Itoi, Kurashiki, all of Japan

[73] Assignee: Shiseido Co., Ltd., Japan

[22] Filed: Feb. 4, 1975

[21] Appl. No.: 546,990

[30] Foreign Application Priority Data

Feb. 24, 1974 Japan ............................. 49-16316

[52] U.S. Cl. .................. 260/676 R; 260/683.9; 424/DIG. 5; 424/47; 424/59; 424/60; 424/64; 424/70
[51] Int. Cl.² ..................... C07C 9/00; C07C 11/00
[58] Field of Search ............... 260/676 R, 683.9; 424/64, 59, 355

[56] References Cited

FOREIGN PATENTS OR APPLICATIONS 897,867   5/1962   United Kingdom ............ 424/68

OTHER PUBLICATIONS

1947–1956 5th Decennial Index, vol. S–Tf, p. 12431S.
Godo, Chem. Abs., 1949, vol. 43, p. 3153.
Jones, Chem. Abs., 1956, vol. 50, p. 2927.
Sax et al., Chem. Abs., 1958, vol. 52, p. 5916.
Sabetay, Chem. Abs., 1956, vol. 50, p. 4765.
The Journal of Org. Chemistry, vol. 23, No. 2, pp. 153 to 162, 1958.
Jones, Chem. Abs., 1956, vol. 50, p. 6752.
Ansart, 1969, vol. 70, p. 216, Chem. Abs.
Ueda et al., 1970, vol. 72, p. 61942, Chem. Abs.

Primary Examiner—Dale R. Ore
Attorney, Agent, or Firm—Paul & Paul

[57] ABSTRACT

A non-irritating base component useful for cosmetics and topical preparations consisting of 2,6,10,15,19,23-hexamethyltetracosane having a high stability and being very safe for use on skin are hereby disclosed. Said component is synthesized by (a) preparing diacetylene dialcohol by reacting at least one ketone selected from the group consisting of 6,10-dimethylundecan-2-one, 6,10-dimethylundeca-3,9-dien-2-one, 6,10-dimethylundeca-5,9-dien-2-one, 6,10-dimethylundeca-5,10-dien-2-one and 6,10-dimethylundeca-3,5,9-trien-2-one, with acetylene and then subjecting the reaction product to the oxidation coupling, or by reacting ketone with diacetylene and (b) hydrocracking the diacetylene dialcohol directly or after hydrogenation.

2 Claims, 2 Drawing Figures

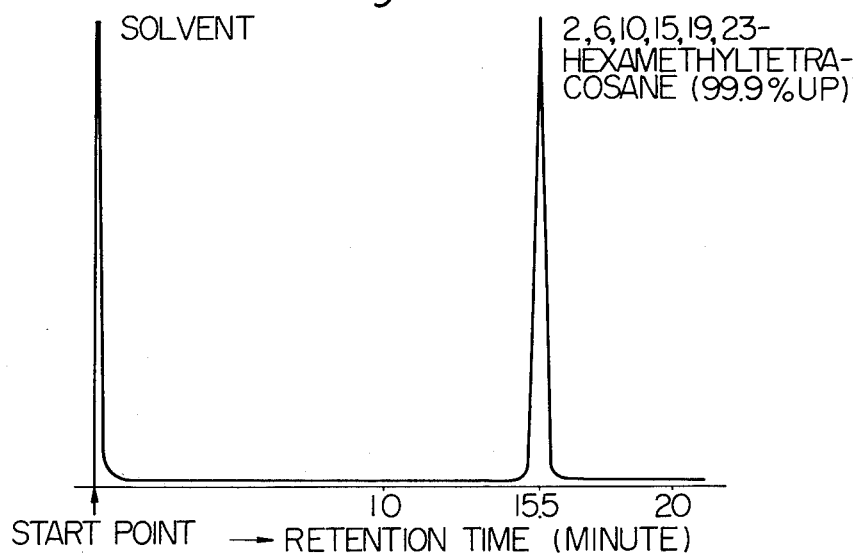
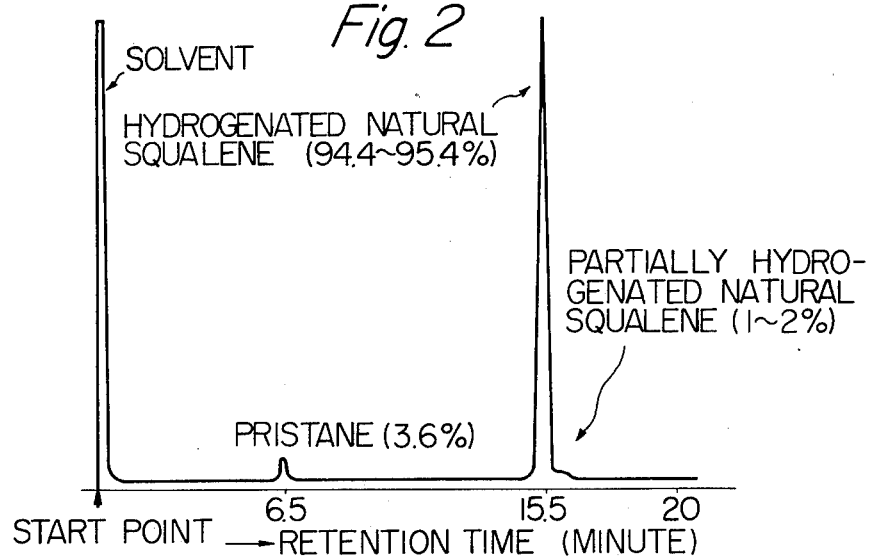

PROCESS FOR PREPARING 2,6,10,15,19,23-HEXAMETHYLTETRACOSANE

BACKGROUND OF THE INVENTION

1. Field of the Invention

The present invention relates to a base component for cosmetics or and topical preparations, more specifically relates to a base component for cosmetics and topical preparations (for example, ointments or the like and also of lesser consistency) consisting of 2,6,10,15,19,23-hexamethyltetracosane.

2. Description of the Prior Art

Most of the conventional base components used for cosmetics or topical preparations are generally compositions obtained from natural products, and these compositions are usually composed of various mixtures. For this reason, when these base components, are incorporated into cosmetics or topical preparations, there are problems of safety from the standpoint of irritation to the human skin, and stability against degradation with the lapse of time cannot be sufficiently assured (short shelflife). Especially, the problem of said stability (that is, the stability to the action of microorganisms, and physical and chemical stabilities) in the base components of the cosmetics or topical preparations is that degradation can result in the cosmetics or topical preparations making it unsafe for use on human skin. The difficulty in finding a solution to this problem of stability is due to the fact that a composition having a constant and uniform quality can not be obtained from natural products.

Heretofore, the conventional cosmetics or topical preparations contain a base component consisting of hydrocarbon oils such as, for example, liquid paraffins, a hydrogenated dipentene polymer obtained from turpentine oil and a hydrogenated squalene obtained from the liver oil of deep-sea sharks. Each of these oils, however, is a mixture of various components and may cause irritation to the human skin and, also, is not sufficiently stable against degradation with time. These are important problems to be solved in cosmetics or topical preparations.

It is known that the hydrogenated squalene is a mixture composed mainly of 2,6,10,15,19,23-hexamethyltetracosane. Although the hydrogenated squalene contains, as impurities, minute amounts of a mixture of partially hydrogenated pristane and squalene, it has heretofore been used in the art as a base component which is a relatively safe with regard to human skin applications. The hydrogenated squalene has a high stability to the action of the microorganisms with time and a high non-irritating property compared with other hydrocarbon oils, both of which properties are important for the base components of the cosmetics or topical preparations. However, since the hydrogenated squalene is obtained from a natural source, minute amounts of the impurities mentioned above are inevitably contained therein and the problems caused by these impurities, that is, physical and chemical changes with time and the resulting reduction of the ability for safe use on human skin, cannot be neglected. Furthermore, since the hydrogenated squalene can be prepared from squalene contained in the liver oil of deep-sea sharks, which is not always readily available, the industrial use of squalene is quantitatively limited.

Due to the above-mentioned circumstances, instead of the hydrogenated squalene, use of hydrogenated products of an isoprene polymer has recently been proposed in several references (for example, Japanese Patent Application Laid-Open No. 48647/73 and German Pat. No. 1117107). However, these products contain a number of isomers, and their qualities are far from satisfactory for the base components of cosmetics and topical preparations. This is due to the fact that a satisfactory technique for the selective polymerization of isoprene, that is, the regulation or control of terminal linkages of isoprene molecules during the course of polymerization, such as head-to-tail linkage or tail-to-tail linkage, has not as yet been established in the art.

SUMMARY OF THE INVENTION

The object of the present invention is to provide a base component for cosmetics and topical preparations consisting of 2,6,10,15,19,23-hexamethyltetracosane having a high stability against degradation with time and a non-irritating property with regard to human skin.

Another object of the present invention is to provide a method for preparing the base component, 2,6,10,15,19,23-hexamethyltetracosane, for cosmetics and topical preparations.

Other objects of the present invention are to provide cosmetics such as, for example, an oil-in-water (o/w) type cream, a water-in-oil (w/o) type cream, a lipstick, solid hair preparations such as, for example, pomade, or the like, bath oil, suntan oil, or the like, and topical preparations such as, for example, a hydrophilic ointment base and an hydrophobic ointment base or the like, both of which comprise a base component effective for protecting the human skin from the action of microorganisms.

In accordance with the present invention, there is provided a non-irritating base component for cosmetics and topical preparations consisting of synthetic 2,6,10,15,19,23-hexamethyltetracosane.

This invention includes a novel process for the synthesis of the base component for cosmetics and topical preparations. More specifically, in accordance with one aspect of this invention, there is provided a process for the preparation of 2,6,10,15,19,23-hexamethyltetracosane, which comprises reacting at least one ketone (see, The Journal of Organic Chemistry, 23, No. 2, pp. 153–157, 1958) selected from the group consisting of 6,10-dimethylundecan-2-one (tetrahydrogeranyl acetone), 6,10-dimethylundeca-3,9-dien-2-one (geranyl acetone), 6,10-dimethylundeca-5,9-dien-2-one (citronellylidene acetone), 6,10-dimethylundeca-5,10-dien-2-one and 6,10-dimethylundeca-3,5,9-trien-2-one (pseudoionone), which are industrially available stereospecific ketones, with acetylene and subjecting the reaction product to the oxidative coupling, or reacting said ketone with diacetylene, to thereby form a novel compound (diacetylene dialcohol), that is, 2,6,10,15,19,23-hexamethyltetracosa-11,13-diyne-10,15-diol, 2,6,10,15,19,23-hexamethyltetracosa-1,6-diene-11,13-diyne-10,15-diol, 2,6,10,15,19,23-hexamethyltetracosa-2,6-diene-11,13-diyne-10,15-diol, 2,6,10,15,19,23-hexamethyltetracosa-2,8-diene-11,13-diyne-10,15-diol, 2,6,10,15,19,23-hexamethyltetracosa-2,6,8-triene-11,13-diyne-10,15-diol, 2,6,10,15,19,23-hexamethyltetracosa-1,6,18,23-tetraene-11,13-diyne-10,15-diol, 2,6,10,15,19,23-hexamethyltetracosa-1,6,18,22-tetraene-11,13-diyne-10,15-diol, 2,6,10,15,19,23-hexamethyltetracosa-1,6,16,22-tetraene-11,13-diyne-10,15-diol, 2,6,10,15,19,23-hexamethyltetracosa-2,6,18,22-tetraene-11,13-diyne-10,15-diol 2,6,10,15,19,23-hexamethyltetracosa-2,6,16,22-tetraene-11,13-diyne-10,15-diol, 2,6,10,15,19,23-hexamethyltetracosa-2,8,16,22-tetraene-11,13-diyne-10,15-diol, 2,6,10,15,19,23-hexamethyltetracosa-1,6,16,18,22-pentaene-11,13,diyne-10,15-diol, 2,6,10,15,19,23-hexamethyltetracosa-2,6,16,18,22-pentaene-11,13-diyne-10,15-diol, 2,6,10,15,19,23-hexamethyltetracosa-2,8,16,18,22-pentaene-11,13-diyne-10,15-diol and 2,6,10,15,19,23-hexamethyltetracosa-2,6,8,16,18,22-hexaene-11,13-diyne-10,15-diol;

and, then, hydrocracking the so obtained diacetylene dialcohol or hydrogenating the diacetylene dialcohol with subsequent hydrocracking of the hydrogenation product to thereby synthesize 2,6,10,15,19,23-hexamethyltetracosane.

According to the synthesis process of this invention, 2,6,10,15,19,23-hexamethyltetracosane of a high purity (not less than 99%) can be prepared efficiently in high yield and at a low cost.

2,6,10,15,19,23-hexamethyltetracosane has the following formula:

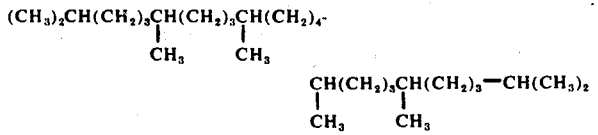

DESCRIPTION OF PREFERRED EMBODIMENT

The present non-irritating base component can be incorporated into cosmetics such as, for example, an oil-in-water type cream, a water-in-oil type cream, a lipstick, a bath oil, a suntan oil, a milky lotion, a hair dressing preparation such as a pomade, an emulsified foundation, a make-up stick, a make-up cake, a pressed powder, a hair conditioner, a hair rinse, and the like, and also incorporated into topical preparations such as, for example, a hydrophilic ointment, a hydrophobic ointment, and the like.

The amount of the present non-irritating base component incorporated into cosmetics or topical preparations can be varied over a wide range depending upon the type of cosmetics and topical preparations. Typical amounts (% by weight) of the base component to be incorporated into cosmetics or topical preparations based upon the total weight of cosmetics or topical preparations, are indicated in the following Table 1.

Table 1

| | |
|---|---|
| o/w type cream | 1 – 50 wt% |
| w/o type cream | 20 – 50 wt% |
| o/w type milky lotion | 1 – 40 wt% |
| w/o type milky lotion | 20 – 40 wt% |
| emulsified foundation | 5 – 20 wt% |
| lipstick | 0.5 – 95 wt% |
| make-up stick | 0.5 – 45 wt% |
| make-up cake | 0.5 – 30 wt% |
| pressed powder | 0.5 – 8.0 wt% |
| hairdressing preparing | |
| solid type | 5 – 30 wt% |
| liquid type | 1 – 30 wt% |
| pomade | 1 – 85 wt% |
| hair conditioner | 1 – about 100 wt% |
| hair rinse | 1 – 15 wt% |
| bath oil | 5 – about 100 wt% |

Table 1-continued

| | |
|---|---|
| suntan oil | 50 – about 100 wt% |
| hydrophilic type ointment | 20 – 50 wt% |
| hydrophobic type ointment | 5 – 90 wt% |

The other cosmetic or topical preparation ingredients used together with the present base component can be those which are contained in the conventional cosmetics and the conventional topical preparations. Such ingredients include surface active agents such as, for example, polyoxyethylene cetyl alcohol ether, polyoxyethylene sorbitan monopalmitate, polyoxyethylene isostearyl alcohol ether, sorbitan monopalmitate and the like; oils such as, for example, fatty acid, white vaseline, silicone oil, mineral oil, ester oil such as di-iso-cetyl adipate, glycerol triisostearate, glycerol monostearate, glycerol tristearate and the like; waxs such as, for example, beeswax, solid paraffin, liquid paraffin, ceresine, microcrystallin wax, lanolin wax, hydrogenated caster oil and the like; humectant such as, for example, higher alcohol, polyethylene glycol, glycerine, 1,3-butylene glycol and the like; pigments; dyes; perfumes; preservatives; lake; ultra violet absorbers; antioxidants; germicide; synthetic polymer such as low molecular weight polyethylene, natural polymer such as gum arabic, tragacanth gum and the like; propellants such as Freon; and the like.

Typical examples of the synthesis of 2,6,10,15,19,23-hexamethyltetracosane will now be described.

SYNTHESIS EXAMPLE 1

Synthesis of 2,6,10,15,19,23-hexamethyltetracosa-2,6,18,22-tetraene-11,13-diyne-10,15-diol:

a. Reaction between geranyl acetone and diacetylene:

A 2l-capacity, 3-neck, round-bottom flask was charged with 1000 ml of liquid ammonia, and 11.5 g of metallic sodium was added thereto. A hydrogen-diluted gas of diacetylene containing about 30 mole % each of acetylene, methylacetylene and vinylacetylene based on diacetylene was blown into the flask, and when the color of the solution of metallic sodium in liquid ammonia changed from bluish green to white, 97 g of geranyl acetone was added to the solution. The reaction was conducted under reflux for 4 hours. After completion of the reaction, 54 g of ammonium chloride was added to the reaction mixture and liquid ammonia was removed by distillation. Then, 500 ml of ethyl ether and 500 ml of water were added to the residue to cause phase separation. The organic layer was washed with water and distillation of the ether gave 121 g of the crude product. As a result of G. P. C. analysis of the crude product, it was observed that the crude product included 44.2 g of 2,6,10,15,19,23-hexamethyltetracosa-2,6,18,22-tetraene-11,13-diyne-10,15-diol.

b. Ethynylation of geranyl acetone to dehydronerolidol and polymerization thereof:

A 2 l-capacity, 3-neck, round-bottom flask was charged with 1000 ml of liquid ammonia and 11.5 g of metallic sodium was added thereto. Acetylene gas was blown into the flask, and when the color of the liquid ammonia solution changed from bluish green to white, 97 g of geranyl acetone was added to the solution and the reaction was conducted under reflux for 4 hours. After completion of the reaction, 54 g of ammonium chloride was added to the reaction mixture and liquid ammonia was removed by distillation. Then, 500 ml of ethyl ether and 500 ml of water were added to the residue to cause phase separation. The organic layer was washed with water and distillation of the ether gave 108 g of dehydronerolidol.

A 5 l-capacity, 3-neck, round-bottom flask was charged with 114.7 g of dehydronerolidol, 305.9 g of ammonium chloride, 191.2 g of cuprous chloride, 765 ml of water and 765 ml of ethyl alcohol, and the mixture was agitated at room temperature for 18 hours while blowing oxygen thereinto. After completion of the reaction, none of the starting reactants were left. The reaction mixture was separated with a centrifuge, and the mother solution was extracted with benzene. Benzene and ethyl alcohol were removed from the organic layer by distillation, and the residue was dissolved in benzene and washed with water. The resulting benzene solution was dried with anhydrous calcium sulfate and the solids were removed from the dried solution by filtration. Distillation of benzene from the benzene solution gave 107.8 g of a viscous liquid of 2,6,10,15,19,23-hexamethyltetracosa-2,6,18,22-tetraene-11,13-diyne-10,15-diol.

SYNTHESIS EXAMPLE 2

Synthesis of 2,6,10,15,19,23-hexamethyltetracosa-2,8,16,22-tetraene-11,13-diyne-10,15-diol:

A 2 l-capacity, 3-neck, round-bottom flask was charged with 1000 ml of liquid ammonia, and 7.0 g of metallic lithium was dissolved in liquid ammonia. Then, 2.5 g of liquefied diacetylene was added to the solution and the mixture was agitated for 30 minutes. Then, 398 g of citronellylidene acetone was added to the mixture and the reaction was conducted for 8 hours under reflux of liquid ammonia. 80 g of ammonium chloride was added to the reaction mixture and liquid ammonia was evaporated. Then, 500 ml of benzene and 500 ml of water were added to the residue to cause phase separation, and the organic layer was washed with water repeatedly until the washings became neutral. Distillation of benzene gave 361 g of the crude product. As a result of G. P. C. analysis of this crude product, it was observed that the crude product included 78.4 g of 2,6,10,15,19,23-hexamethyltetracosa-2,8,16,22-tetraene-11,13-diyne-10,15-diol.

SYNTHESIS EXAMPLE 3

Synthesis of 2,6,10,15,19,23-hexamethyltetracosa-11,13-diyne-10,15-diol:

The ethynylation reaction was carried out in the same manner as in Synthesis Example 1-(b) except that 101 g of tetrahydrogeranyl acetone was used instead of geranyl acetone, to thereby obtain 123 g of 3,7,11-trimethyldodecene-1-yne-3-ol.

Then, the oxidative coupling reaction was conducted in the same manner as in Synthesis Example 1-(b) except that 116 g of 3,7,11-trimethyldodecene-1-yne-3-ol was used instead of dehydronerolidol, to thereby obtain 113 g of 2,6,10,19,23-hexamethyltetracosa-11,13-diyne-10,15-diol.

SYNTHESIS EXAMPLE 4

Synthesis of 2,6,10,15,19,23-hexamethyltetracosane starting from the product of Synthesis Examples 1 and 2:

50 ml of ethyl alcohol and 2.5 g of a palladium-carbon catalyst formed by depositing 5% of metallic palladium on active carbon (hereinafter referred to as "Pd/C") were added to 50 g of 2,6,10,15,19,23-hexamethyltetracosa-2,6,18,22-tetraene-11,13-diyne-10,15-diol, and the reaction was conducted at a temperature of 100° C under a hydrogen pressure of 5 to 3 Kg/cm² until absorption of hydrogen was completed.

After the catalyst was removed by filtration and ethyl alcohol was distilled-off, a mixture of 46 g of 2,6,10,15,19,23-hexamethyltetracosa-10,15-diol 4.0 g of 2,6,10,15,19,23-hexamethyltetracosa-10-ol and 0.48 g of 2,6,10,15,19,23-hexamethyltetracosane was obtained. After the mixture was mixed with 1.0 g of a nickel-diatomaceous earth catalyst (having a nickel content of about 50% by weight), 2.5 g of silica-alumina (having an alumina content of 30% by weight) and 100 ml of n-heptane (solvent), hydrocracking reaction was carried out at a temperature of 230° C under a hydrogen pressure of 100 Kg/cm² for 16 hours. The reaction mixture was cooled, and the solids were removed by filtration, and n-heptane was removed from the filtrate to obtain 47 g of crude 2,6,10,15,19,23-hexamethyltetracosane. The crude product was distilled under reduced pressure and 45 g of pure 2,6,10,15,19,23-hexamethyltetracosane was obtained at a boiling point range of 190 to 195° C under 0.5 mm/Hg.

SYNTHESIS EXAMPLE 5

Synthesis of 2,6,10,15,19,23-hexamethyltetracosane starting from the product of Synthesis Example 3:

The reaction was conducted in the same manner as in Synthesis Example 4 except that 2,6,10,15,19,23-hexamethyltetracosa-11,13-diyne-10,15-diol was used instead of 2,6,10,15,19,23-hexamethyltetracosa-2,6,18,22-tetraene-11,13-diyne-10,15-diol, and 47 g of crude 2,6,10,15,19,23-hexamethyltetracosane was obtained.

The so obtained crude product was subjected to distillation under reduced pressure and a fraction boiling at 190° to 195° C under 0.5 mm/Hg was recovered to obtain 45 g of pure 2,6,10,15,19,23-hexamethyltetracosane.

FIG. 1 illustrates a chart of the gas chromatography of 2,6,10,15,19,23-hexamethyltetracosane prepared by this invention.

FIG. 2 illustrates a chart of the gas chromatography of hydrogenated natural squalene.

Gas Chromatography Measurement Conditions are as follows.

Device: Varian Aerograph 1200
Liquid phase: silicone SE-30, 3%
Solid phase: Chromosolve WAW-DMCS, 80 – 100 mesh
Column length: 5 feet
Column diameter: ⅛ inch
Temperature elevation: 100°– 108° per minute
Detector: F. I. D.
Gas flow rates: $N_2$ = 30 ml/min, $H_2$ = 30 ml/min, air = 300 ml/min
Injection temperature: 290° C
Detection temperature: 325° C
Chart speed: 1 cm/min
Solvent: n-hexane 2,6,10,15,19,23-Hexamethyltetracosane of this invention, either by itself or when combined with other cosmetic or topical preparation constituents, has excellent properties which is a prerequisite of the base component for cosmetics and topical preparations, such as stability against degradation with the lapse of time, and high and durable safety with regard to human skin. In order to prove this fact, we tested the compound for irritative and toxic properties. More specifically, we made tests for primary irritation to the skin, the accumulated irritation, the irritation to eyelids and the acute toxicity using test animals (rabbits, guinea pigs and rats) and after we had sufficiently confirmed the safety of the compound by these animal tests, we conducted closed patch test and the excitation test on the skin of healthy women. As a result of these tests, we confirmed the safety of the compound of this invention.

As the test for determination of the stability against physical and chemical degradation with the lapse of time, we conducted investigations of the changes in peroxide value of the compound by bubbling air at a temperature of 120° C and undertook tests whether there were changes in the skin irritating to animal skin. As the test for determination of the stability against microbial degradation with the lapse of time, the propagation test was carried out by using *Pseudomonas aeruginosa* and Pseudomonas strain No. 23 (unidentified) to compare 2,6,10,15,19,23-hexamethyltetracosane of this invention with conventional hydrogenated squalene with respect to the degree of metabolization by the microorganisms.

Test procedures and results of each of the foregoing tests will now be described.

1. Examination of Primary Irritation on Rabbits

Test Method:

Albino rabbits having a body weight of 2.3 to 3 Kg were used as test animals. Eight rabbits were shorn on the back by electric clippers, and they were divided into two groups, each consisting of 4 rabbits. The two groups of rabbits were fixed by bareness with one group being abraded and the other group was tested as clipped.

A sample to be tested was applied on a lint cloth having a size of 2.5 cm × 2.5 cm, and the lint cloth was placed on the skin of the rabbits and covered with gauze having a size of 3.5 cm × 3.5 cm. After 24 hours, the lint cloth was removed and the degree of irritation of the sample to the skin was evaluated by observing the degree of appearance of erythema and edema and rating these according to the following scales, and determining the final score based on the sum of the observation points.

Scoring Criteria:

(1) Erythema and Desquamation:

| | Observation Point |
|---|---|
| no erythema | 0 |
| slight erythema | 1 |
| obvious erythema | 2 |
| strong erythema | 3 |
| strong erythema with slight desguamation | 4 |

(2) Edema:

| | Observation Point |
|---|---|
| no edema | 0 |
| very slight edema | 1 |
| slight edema | 2 |
| medium edema (about 1 mm) | 3 |
| strong edema (extending beyond applied region) | 4 |

Evaluation of Sample:

| Sum of Observation points of 8 Rabbits | Evaluation |
|---|---|
| 8 or smaller | no substantial irritation |
| larger than 8 | irritation |

2. Examination of Accumulated Irritation on Guinea Pig Skins

Text Method:

The test was conducted in the same manner as described above except that the test samples were patched tested on the skin for 3 days. The reactions were evaluated according to the scoring (1) mentioned above. The results of the tests are shown in Table 2.

Table 2

| Compound Tested | POV[2] Value | Primary Irritation on Rabbit Skin | Accumulated Irritation on Guinea Pig Skin |
|---|---|---|---|
| Comparative Examples | | | |
| pristane isolated from hydrogenated squalene | 0.1 | 18/8 | 32/8 |
| hydrogenated squalene | 0.2 | 0/8 | 3/8 |
| hydrogenated squalene air-bubbled at 120° C for 2 hours [1] | 4.0 | 2/8 | 7/8 |
| hydrogenated squalene air-bubbled at 120° C for 4 hours | 28.0 | 6/8 | 17/8 |
| hydrogenated squalene air-bubbled at 120° C for 6 hours | 130.0 | 15/8 | 25/8 |
| Examples of This Invention | | | |
| 2,6,10,15,19,23-hexamethyltetracosane | 0 | 0/8 | 1/8 |
| 2,6,10,15,19,23-hexamethyltetracosane air-blown at 120° C for 4 hours | 0.6 | 0/8 | 1/8 |
| 2,6,10,15,19,23-hexamethyltetracosane air-blown at 120° C for 6 hours | 2.4 | 1/8 | 4/8 |

Notes:
1. Test for Physical and Chemical Changes with Time:
 2. Air was bubbled into the sample at 120° C to cause autooxidation, and the oxidized oil was collected after the prescribed period had passed. The peroxide value was measured as a factor indicating the degree of oxidation.
2. POV Value (peroxide value):

Precisely measured 500 to 1000 mg of a sample was charged into a amber-colored flask, and 20 ml of a 1 : 2 mixture of acetic acid: chloroform was added thereto as a solvent. The inside pressure of the flask was reduced and nitrogen gas was substituted for the air in the flask. Then, 2 ml of a saturated solution of potassium iodide in methanol was added to the charge in the flask and the flask was kept in the dark at 37° C for 30 minutes (the flask was shaken occasionally). Then, 30 ml of water was added and titration was conducted with a 0.01N solution of sodium thiosulfate ($Na_2S_2O_3$). The point at which the yellow color of iodine disappearred was determined as the neutralization point. The above procedures were repeated without addition of the sample to obtain a blank value. The peroxide value (meq/Kg) was calculated according to the following equation:

$$\text{POV value (meq/Kg)} = \frac{[0.01\text{N Na}_2\text{S}_2\text{O}_3 \text{ (ml)} - 0.01\text{N Na}_2\text{S}_2\text{O}_3 \text{ (ml) in blank}]}{\text{sample (mg)} \times 10^4}$$

As is apparent from the results shown in Table 2, 2,6,10,15,19,23-hexamethyltetracosane of this invention does not irritate the skin either as it is or after being subjected to the accelerated stability test, and it can be used very effectively as a base component for cosmetics or topical preparations.

Pristane isolated from hydrogenated natural squalene is a very strong irritant to animal skin, and apparently, it is a mixture not suitable for use as a base component for cosmetics or topical preparations. In the test for physical and chemical changes with the lapse of time (the accelerated stability test), hydrogenated squalene exhibits large variations of peroxide value, and an increase of the animal skin-irritating property by these changes of the hydroxyl value cannot be neglected. It is apparent that this undesirable phenomenon is due to the presence of a partial hydrogenation product of squalene, and it will readily be understood that this partially hydrogenated squalene is also a mixture unsuitable as a base component for cosmetics or topical preparations. In other words, it is only the pure 2,6,10,15,19,23-hexamethyltetracosane that is expected to give a satisfactory non-irritating property to cosmetics or topical preparations, and the most important feature of this invention is in the removal of the impurities.

With respect to the 2,6,10,15,19,23-hexamethyltetracosane of this invention, we further conducted the eyelid-irritant test (periodical measurement of cornea, iris and conjunctivea), the test for acute toxicity on oral administration (more than 25 ml/Kg) and the test of the irritative property to the human skin (20 healthy women) and, as a result, we confirmed that the 2,6,10,15,19,23-hexamethyltetracosane of this invention has a satisfactory non-irritating property.

The method of the test of microbial degradation with the lapse of time and results of this test will now be described.

The above-mentioned *Pseudomonas aerginosa* and Pseudomonas strain No. 23 (unidentified) were used as test microorganisms. Other conditions of the test were as follows.

1. Composition of Culture Medium:

2.5 g of K$_2$NPO$_4$, 0.5 g of KH$_2$PO$_4$, 0.3 g of MgSO$_4$, 0.3 g of CaCl$_2$, 3.0 g of (NH$_4$)$_2$SO$_4$, 0.3 g of NaCl, 10 g of a compound to be tested, and 1 l of water.

2. Culture Conditions:

30 ml of a culture medium was charged into a 100 ml-capacity shaking flask, and sterilized in an autoclave. After cooling, the culture medium was inoculated with one platinum-spoonful of a suspension of the pre-cultured microorganism and the culture was shaken at 30° C for 7 days at a frequency of 120 cycles per minute.

3. Measurement of Propagation of Cells: 2 ml of a 0.006% dilute solution of Rapisol and 2 to 4 drops of 1N H$_2$SO$_4$ were added to 2 ml of the culture medium, and sufficiently mixed. The mixture was subjected to centrifugal separation, and the precipitate was washed with petroleum ether and subjected to centrifugal separation again. The recovered precipitate was suspended in 5 ml of water, and the absorption at 660 m$\mu$ was determined by a spectrophotometer to determine the degree of propagation of cells.

4. Evaluation:

When the cosmetic base component of this invention was tested according to the above-mentioned test method, it was observed that the metabolization was negative to each of the microorganisms tested.

As is apparent from the foregoing, the base component of this invention has no irritating property to the skin of animals and human skin, either as it is or after it has been subjected to the accelerated stability test, and it also has excellent stability against microbial degradation with time. Accordingly, it is an ideal base component for cosmetics and topical preparations, and it is apparent the base component of this invention has high stability against degradation with time and is very safe for use on human skin.

This invention will now be illustrated in detail by reference to the following Examples in which the excellent effects of cosmetics and topical preparations having the base component of this invention over conventional cosmetics and topical squalene are demonstrated. Of course, these Examples by no means limits the scope of this invention.

EXAMPLE 1

An O/W type cream was prepared by the following procedure.

| | Components | % by weight |
|---|---|---|
| (I) | 2,5,10,15,19,23-hexamethyltetracosane | 14 |
| | cetyl alcohol | 3 |
| | purified white vaseline | 5 |
| | di-iso-cetyl adipate | 2 |
| (II) | polyoxyethylene cetyl alcohol ether | 3 |
| | polyethylene glycol | 2 |
| | water (de-ionized water) | 71 |
| (III) | perfume | suitable amount |
| | preservative | suitable amount |

The above components (I) were mixed and melted with stirring at a temperature of 50° to 60° C, the components (II) were added to the melted mixture and suitable amounts of the components (III) were added thereto to form the product. A sample for the comparative test was prepared in the same manner as mentioned above except that the components (III) were not incorporated.

EXAMPLE 2

A W/O type cream was prepared by the following procedure.

| | Components | % by weight |
|---|---|---|
| (I) | 2,6,10,15,19,23-hexamethyltetracosane | 40 |
| | purified beeswax | 12 |
| | di-isocetyl adipate | 8 |
| (II) | sorbitan monopalmitate | 3 |
| | polyoxyethylene sorbitan monopalmitate | 1 |
| | water (de-ionized) | 36 |
| (III) | perfume | suitable amount |

-continued

| Components | % by weight |
|---|---|
| preservative | suitable amount |

A product was prepared in the same manner as in Example 1, and a sample for the comparative test was similarly prepared without incorporation of the components (III).

EXAMPLE 3

A solid hair preparation (pomade) was prepared by the following procedure.

| | Components | % by weight |
|---|---|---|
| (I) | 2,6,10,15,19,23-hexamethyltetracosane | 9 |
| | purified white vaseline | 52 |
| | solid paraffin | 6 |
| | glycerol triisostearate | 30 |
| (II) | dye | suitable amount |
| (III) | perfume | 3 |

The components (I) were heated and melted with stirring to obtain a homogeneous mixture. Then, the component (II) was added to the melted mixture to color the mixture. When the temperature of the mixture was lowered to some extent, the component (III) was added thereto, followed by agitation. The resulting homogeneous mixture was poured into a vessel and then cooled and solidified to obtain the product. A sample for the comparative test was similarly prepared without incorporation of the components (II) and (III).

EXAMPLE 4

A lipstick was prepared by the following procedure.

| | Components | % by weight |
|---|---|---|
| (I) | 2,6,10,15,19,23-hexamethyltetracosane | 20 |
| | glycerol triisostearate | 35 |
| | ceresine (hydrocarbon wax) | 20 |
| | microcrystalline wax (hydrocarbon wax) | 5 |
| | purified hydrogenated wool wax | 10 |
| (II) | lake (pigment : glycerol isostearate- 1 : 1) | 10 |
| | dye solution | suitable amount |
| | perfume | suitable amount |

The components (I) were mixed and melted, at a temperature of 95° to 100° C, and the components (II) were added to the melted mixture and blended therewith. The mixture was molded into a product by means of a lipstick molding machine. A sample for the comparative test was similarly prepared without incorporation of the components (II).

EXAMPLE 5

A bath oil was prepared by the following procedure.

| Components | % by weight |
|---|---|
| 2,6,10,15,19,23-hexamethyltetracosane | 50 |
| diisocetyl adipate | 25 |
| glycerol triisostearate | 15 |
| polyoxyethylene isostearyl alcohol ether | 5 |
| perfume | 5 |

The above components were mixed and agitated at a temperature of 40° C to obtain the product. A sample for the comparative test was similarly prepared without incorporation of the perfume component.

EXAMPLE 6

An aerosol type suntan oil was prepared by the following procedure.

| | Components | % by weight |
|---|---|---|
| (I) | 2,6,10,15,19,23-hexamethyltetracosane | 27.3 |
| | glycerol tri-iso-stearate | 3.5 |
| | di-iso-cetyl adipate | 3.5 |
| (II) | ultraviolet absorber | 0.525 |
| | perfume | 0.175 |
| (III) | Freon 11 | 26.0 |
| | Freon 12 | 39.0 |

The components (I) and (II) were mixed with stirring at room temperature, the mixture was poured into an aerosol container and the propellants (III) were filled into the container to obtain the product. A sample for the comparative test was prepared without using components (II) and (III).

EXAMPLE 7

A hydrophilic ointment base was prepared by the following procedure.

| Components | % by weight |
|---|---|
| 2,6,10,15,19,23-hexamethyltetracosane | 32 |
| glycerol triisostearate | 35 |
| glycerol monostearate | 20 |
| glycerol tristearate | 5 |
| hydrogenated castor oil | 5 |
| polyoxyethylene sorbitan monostearate | 3 |

The above components were mixed and heated to a temperature of 80° to 90° C with stirring, and the mixture was cooled to room-temperature to obtain the product.

EXAMPLE 8

An hydrophobic ointment base was prepared by the following procedure.

| Components | % by weight |
|---|---|
| 2,6,10,15,19,23-hexamethyltetracosane | 66 |
| low molecular weight polyethylene (having a molecular weight of about 1000) | 19 |
| purified solid paraffin | 15 |

The above components were mixed and heated to a temperature of 80° to 90° C with stirring, and the mixture was cooled to room-temperature to obtain the product.

COMPARATIVE EXAMPLES 1 to 6

Samples for the comparative test were prepared in the same manner as in Examples 1 to 6 except that hydrogenated squalene was used instead of 2,6,10,15,19,23-hexamethyltetracosane.

Samples for the comparative test prepared in Examples 1 to 6 and Comparative Examples 1 to 6 were subjected to the accelerated stability test under the following conditions to obtain results shown in Table 3.

Accelerated Stability Test Conditions:

Samples were allowed to stand for 40 hours at 40° C under the radiation of carbon arc lamp in a Fade-Ometer. Allowing the samples to stand under these conditions is comparable to the samples standing under a midsummer sun for 28 days.

Table 3

| Test Sample | Change of Odor at Accelerated Stability Test* | | | Irritation on Skins of Guinea Pigs | |
| --- | --- | --- | --- | --- | --- |
| | no change | slight change | obvious change | just after preparation | after accelerated stability test |
| Example 1 | 8 | 2 | 0 | 1/8 | 2/8 |
| Comparative Example 1 | 0 | 4 | 6 | 1/8 | 8/8 |
| Example 2 | 7 | 3 | 0 | 2/8 | 2/8 |
| Comparative Example 2 | 0 | 1 | 9 | 2/8 | 9/8 |
| Example 3 | 10 | 0 | 0 | 1/8 | 1/8 |
| Comparative Example 3 | 1 | 8 | 2 | 1/8 | 8/8 |
| Example 4 | 2 | 7 | 1 | 1/8 | 1/8 |
| Comparative Example 4 | 0 | 1 | 9 | 1/8 | 8/8 |
| Example 5 | 6 | 4 | 0 | 3/8 | 4/8 |
| Comparative Example 5 | 0 | 3 | 7 | 3/8 | 11/8 |
| Example 6 | 9 | 1 | 0 | 2/8 | 2/8 |
| Comparative Example 6 | 0 | 7 | 3 | 2/8 | 9/8 |

* A standard sample was used that had been stored in the dark in a tank with a thermostat, maintained at 25° C, since immediately after preparation. The change of the odor was determined by a panel of 10 experts. The standard sample and the sample subjected to the accelerated test were applied on the skin of guinea pigs in a constant temperature room maintained at 25° C, and their odors were compared.

In addition to the items shown in Table 3, the change of color by the acclerated stability test was examined. Though color changes were observed in some samples prepared in the Comparative Examples, the changes were not so conspicuous as the changes in odor and the skin-irritating property.

As is apparent from Tables 2 and 3, the 2,6,10,15,19,23-hexamethyltetracosane of this invention is a base component for cosmetics or topical preparations which has excellent stability against degradation with time and is very safe for use on human skin, and even though it is incorporated in a cosmetic or topical preparations, it has high stability and is very safe for use on human skin. More specifically, the change in order such as observed in the case of hydrogenated squalene is not observed in the case of the cosmetic or topical preparations containing the base component of this invention as is proven by the above-mentioned panel test (see, Table 3). Further, as is apparent from the foregoing results of the test for irritation on the skin of guinea pigs subjected to the acclerated stability test, the cosmetic composition containing the base component of this invention has a much higher and more better stability than cosmetics comprising of hydrogenated natural squalene.

What we claim is:

1. A process for preparing 2, 6, 10, 15, 19, 23-hexamethyltetralosane, comprising the steps of:
   a. preparing diacetylene dialcohol (i) by reacting at least one ketone selected from the group consisting of 6, 10-dimethylundecan-2-one, 6, 10-dimethylundeca-3, 9-dien-2-one, 6, 10-dimethylundeca-5, 9-dien-2-one, 6, 10-dimethylundeca-5, 10-dien-2-one and 6, 10-dimethylundeca-3, 5, 9-trien-2-one with acetylene in liquid amonia in the presence of metallic sodium under reflux of liquid ammonia condition and then subjecting the reaction product to the oxidative coupling in the presence of cuprous chloride at room temperature while blowing oxygen thereinto or (ii) by reacting said ketone with diacetylene in liquid ammonia in the presence of at least one metal selected from the group consisting of metallic sodium and metallic lithium under reflux of liquid ammonia condition;
   b. hydrocracking the diacetylene with hydrogen in the presence of a nickel catalyst.

2. The process as claimed in claim 1, wherein said diacetylene prepared in the step (i) or (ii) is further hydrogenated with hydrogen in the presence of metallic palladium catalyst prior to said hydrocracking.

* * * * *

UNITED STATES PATENT OFFICE
CERTIFICATE OF CORRECTION

Patent No. 4,032,588          Dated June 28, 1977

Inventor(s) Kenichi Tomita, Toshiaki Shibuya, Suzuko Koshiba and Kazuo Itoi

It is certified that error appears in the above-identified patent and that said Letters Patent are hereby corrected as shown below:

In the Abstract, line 5, "component" should be --compound--

Column 3, line 64, "preparing" should be --preparation--.

Column 6, line 57, "108°" should be -- 108°C --.

Column 9, line 53, "$K_2NPO_4$" should be -- $K_2HPO_4$ --.

Column 10, line 31, after the word "topical", add -- preparations containing hydrogenation products of natural -- .

Column 14, line 6, "order" should be -- odor --.

Column 14, line 19, "hexamethyltetralosane" should be -- hexamethyltetracosane -- .

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*